(12) United States Patent
DeSilva et al.

(10) Patent No.: US 10,031,032 B2
(45) Date of Patent: Jul. 24, 2018

(54) ACOUSTIC MEASUREMENT SYSTEM INCORPORATING A HYBRID WAVEGUIDE PROVIDING THERMAL ISOLATION

(71) Applicant: Siemens Energy, Inc., Orlando, FL (US)

(72) Inventors: Upul P. DeSilva, Oviedo, FL (US); Heiko Claussen, North Brunswick, NJ (US)

(73) Assignee: SIEMENS ENERGY, INC., Orlando, FL (US)

( * ) Notice: Subject to any disclaimer, the term of this patent is extended or adjusted under 35 U.S.C. 154(b) by 392 days.

(21) Appl. No.: 14/800,763

(22) Filed: Jul. 16, 2015

(65) Prior Publication Data

US 2017/0016779 A1  Jan. 19, 2017

(51) Int. Cl.
  *G01K 11/24*  (2006.01)
  *G01N 29/22*  (2006.01)
  *G01K 13/02*  (2006.01)

(52) U.S. Cl.
  CPC .......... *G01K 11/24* (2013.01); *G01K 13/02* (2013.01); *G01N 29/227* (2013.01); *G01N 29/228* (2013.01); *G01K 2013/024* (2013.01); *G01K 2205/00* (2013.01)

(58) Field of Classification Search
  CPC ........ G10K 11/24; G10K 11/22; G10K 13/02; G10K 2013/024; G10K 2205/00; G01N 29/02; G01N 29/04; G01N 29/222; G01N 29/228; G01N 29/227; G01N 29/22
  USPC .................. 73/617, 644, 590, 24.06, 861.18; 374/119
  See application file for complete search history.

(56) References Cited

U.S. PATENT DOCUMENTS

| | | | | |
|---|---|---|---|---|
| 4,153,894 A | * | 5/1979 | Alphonse ............ | G01S 7/52046 181/175 |
| 4,779,452 A | * | 10/1988 | Cohen-Tenoudji .... | G01N 11/00 73/54.41 |
| 4,982,386 A | | 1/1991 | Henriguez | |
| 5,777,230 A | * | 7/1998 | Vandervalk ........... | B06B 1/0662 73/1.82 |
| 6,322,897 B1 | | 11/2001 | Borchert | |
| 6,349,599 B1 | * | 2/2002 | Lynnworth .......... | G01N 29/223 73/644 |
| 8,511,424 B2 | | 8/2013 | Ao | |
| 8,746,399 B2 | | 6/2014 | Ao | |
| 2007/0131034 A1 | * | 6/2007 | Ehlert .............. | A61B 17/32006 73/617 |

(Continued)

FOREIGN PATENT DOCUMENTS

GB  2114295 A  *  8/1983  .........  G01S 7/52047

*Primary Examiner* — Manish S Shah
*Assistant Examiner* — Rose M Miller (57) ABSTRACT

A gas turbine engine including a hybrid waveguide for placement adjacent a flow path for hot combustion gases in the engine is presented. The waveguide includes first and second opposing ends and a first section formed of a first material extending from a transition region to the first end and a second section formed of a second material extending from the transition region to the second end. The first material is a metal or a ceramic and the second material is an electrically isolating material having a lower thermal conductivity than the material of the first section. A membrane may be used to isolate a cavity of the waveguide from combustion gas.

19 Claims, 4 Drawing Sheets

(56) References Cited

U.S. PATENT DOCUMENTS

| | | | |
|---|---|---|---|
| 2012/0266679 A1* | 10/2012 | Ao | ........................ G01F 1/662 73/644 |
| 2014/0064326 A1 | 3/2014 | Claussen | |
| 2015/0030871 A1 | 1/2015 | Bruck | |
| 2015/0063411 A1 | 3/2015 | DeSilva | |
| 2015/0168190 A1 | 6/2015 | DeSilva | |
| 2015/0168230 A1 | 6/2015 | DeSilva | |
| 2016/0273973 A1* | 9/2016 | Larsen | ................... G01K 11/22 |

* cited by examiner

ACOUSTIC MEASUREMENT SYSTEM INCORPORATING A HYBRID WAVEGUIDE PROVIDING THERMAL ISOLATION

RELATED APPLICATION

This application is related to subject matter disclosed in U.S. patent application Ser. No. 14/800,756 filed Jul. 16, 2015

FIELD OF THE INVENTION

The present invention relates to turbine engines and, more particularly, to turbine engines incorporating systems and methods for determining combustion gas temperature based on measurement of acoustic signals. In one application such temperature measurement is used to control operation of a gas turbine engine.

BACKGROUND OF THE INVENTION

Combustion turbines, such as gas turbine engines, generally comprise a compressor section, a combustor section, a turbine section and an exhaust section. In operation, the compressor section can induct and compress ambient air. The combustor section generally may include a plurality of combustors for receiving the compressed air and mixing it with fuel to form a fuel/air mixture. The fuel/air mixture is combusted by each of the combustors to form a hot working gas that may be routed to the turbine section where it is expanded through alternating rows of stationary airfoils and rotating airfoils and used to generate power that can drive a rotor. The expanding gas exiting the turbine section can be exhausted from the engine via the exhaust section.

The fuel/air mixture at the individual combustors is controlled during operation of the engine to maintain one or more operating characteristics within a predetermined range, such as, for example, to maintain a desired efficiency and/or power output, control pollutant levels, prevent pressure oscillations and prevent flameouts. In a known type of control arrangement, a bulk turbine exhaust temperature may also be monitored as a parameter indicative of a condition in the combustor section. For example, a controller may monitor a measured turbine exhaust temperature relative to a reference temperature value, and a measured change in temperature may result in the controller changing the fuel/air ratio at the combustor section.

In a known temperature monitoring system for controlling combustion operations, temperature monitors, such as thermocouples, are located directly in the exhaust flow of the turbine. Such monitoring systems have generally required locating thermocouples at different fixed axial locations along the exhaust flow, which may introduce uncertainties in relation to temperature calculations for controlling the engine as conditions affecting operation of the engine change, such as a varying load condition on the engine.

BRIEF DESCRIPTION OF THE DRAWINGS

An understanding of the invention will be had by reading the following detailed description in conjunction with the accompanying drawings, wherein.

DETAILED DESCRIPTION OF THE INVENTION

The invention is illustrated for an embodiment of a gas turbine engine 10 comprising an acoustic temperature measurement system which determines temperatures of exhaust combustion gas along a flow path extending from the combustor section through the turbine section. As described in Patent Application Publication US 2015/0063411, (assigned to the assignee of the present invention, filed Sep. 4, 2013 and incorporated herein by reference) systems which measure the temperature of a gas are useful for monitoring and control of engine operations. However, due to the high temperatures present in segments of the flow path of the combustion gas, it has been difficult to provide accurate temperature measurements on a long term.

More recently, indirect temperature measurements have been accomplished with acoustic methods to avoid placing temperature probes directly within the hot combustion gas flow. Because engine noise can hinder accurate detection of sound signals transmitted for time of flight measurements, these systems have generated sound signals, distinct and recognizable from sounds normally produced by the engine, to identify acoustic measurement signals that have traveled through the gas flow path. This imposes a high temperature constraint for the acoustic sensors which can be addressed by injection of cooling gas to control the temperature of sensor operation. However, such cooling can affect the time of flight measurements performed. Embodiments of the invention do not require flow of cooling fluid into the measurement region to protect acoustic sensors.

Figure 1:
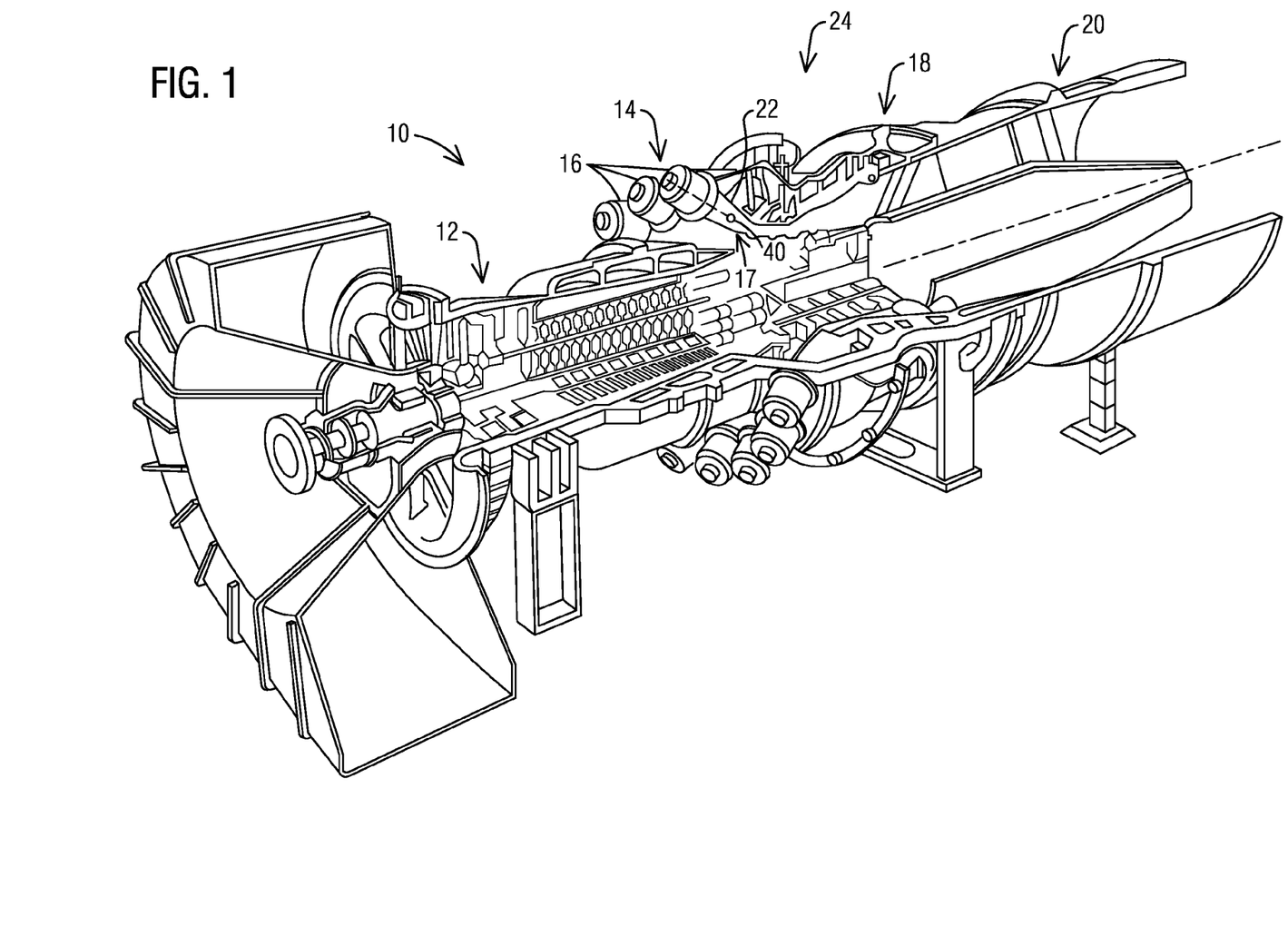
FIG. 1 is a perspective cross-sectional view of a gas turbine engine incorporating an acoustic temperature measurement system in accordance with the present invention.

Referring to FIG. 1, a portion of an exemplary gas turbine engine 10 includes a compressor section 12, a combustor section 14, a turbine section 18, and an exhaust section 20. The combustor section 14 includes a plurality of combustor baskets or combustors 16 and associated transition ducts 22, wherein the combustors 16 and transition ducts 22 define a portion of a flow path 17 along an axial direction in which the combustion gas flows to the exhaust section 20.

During operation of the engine 10, air output from the compressor section 12 is provided to the combustor section 14 where it is combined with fuel in the combustors 16, and the fuel/air mixture is ignited to form the hot combustion gas which is expanded through the turbine section 18 and then passed through the exhaust section 20.

Figure 2:
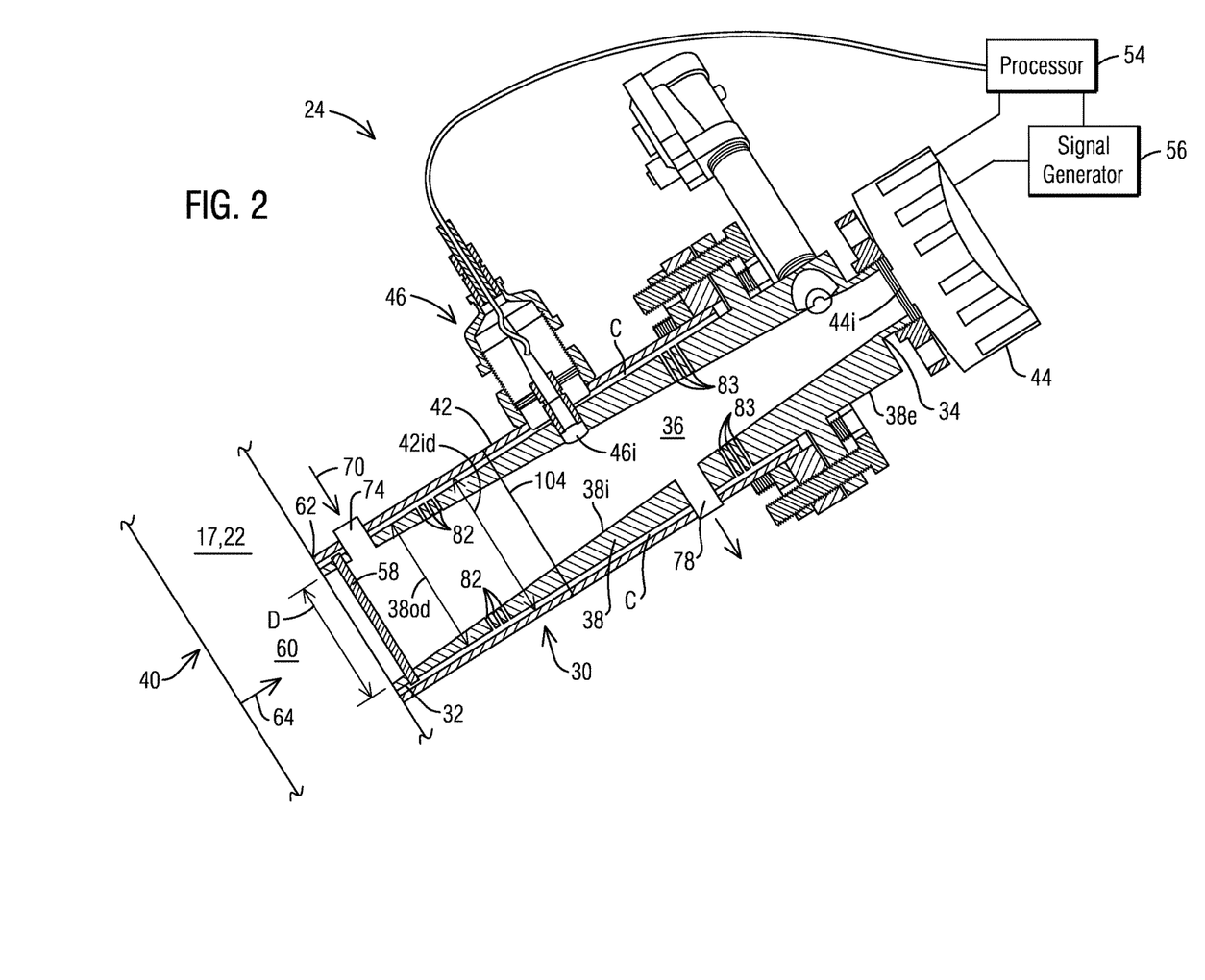
FIG. 2 illustrates features of an acoustic measurement system for determining operating temperature of a combustion gas based on time of flight for an acoustic signal passing through a combustion gas flow path.

Embodiments of the invention incorporate an acoustic temperature measurement system 24 in the gas turbine engine 10 to determine combustion gas temperatures and control operation of the engine 10 such as, for example, by varying the air-to-fuel ratio. The partial view of FIG. 2 illustrates a waveguide 30 in the acoustic temperature measurement system 24 having a body in which there is formed a tapered, e.g., frustoconical, cavity 36 extending between first and second waveguide ends 32, 34. The wall 38 of the body of the waveguide, formed about the cavity 36, has a cylindrically shaped exterior wall surface 38e and has, along an interior surface 38i, a tapered shape complementary to that of the tapered cavity 36.

In the example illustration the waveguide 30 adjoins a transition duct 22 adjacent the combustor section 14 in the turbine 10. More generally, the gas turbine engine 10 may comprise a plurality of waveguides 30, each located at a position of interest along a wall 40 in the flow path 17, including positions within the turbine section or along the wall of a diffuser. The first waveguide end 32 is positioned within a cylindrically shaped mounting sleeve 42 that extends outward from the wall 40. The second waveguide end 34 extends beyond the mounting sleeve 42. As shown in FIG. 2, the mounting sleeve may have an inside diameter $42_{id}$ substantially larger (e.g., 0.5 to one mm) than the outside diameter $38_{od}$ of the cylindrically shaped exterior wall 38 of the waveguide 30. This spaced arrangement provides a channel, C, between the mounting sleeve 42 and the waveguide exterior wall surface 38e.

A pair of acoustic transducer units, i.e., a transmitter unit 44 and a receiver unit 46, are mounted to the waveguide 30. In other embodiments, the waveguide may comprise one or more acoustic transceivers or multiple transmitters or multiple receivers. The transmitter unit 44 includes an inner portion 44i and the receiver unit 46 includes an inner sensor portion 46i that acoustically interfaces with the cavity 36 to emit acoustic signals into the cavity or to sense acoustic signals from the cavity. The transmitter unit 44 is mounted along the second waveguide end 34. The receiver unit 46 is attached to the mounting sleeve 42, e.g., approximately midway between the waveguide ends, and extends through the sleeve, into the waveguide 30 to sense the acoustic signals in the cavity 36 generated by the transmitter unit 44 and reflected back into the waveguide.

The transmitter unit 44 and the receiver unit 46 are each connected to a processor or controller 54 that is configured to operate a signal generator 56 to produce predetermined output signals from the transmitter and to receive time-of-flight signals, corresponding to the output signals, from the receiver unit 46. The controller 54 is further configured to store and process data corresponding to the received signals to calculate temperatures and to produce outputs in accordance with the calculated temperatures associated with the received signals, as described with detail in US Pub. 2015/0063411. The controller 54 may also be configured to provide signals for controlling operations affecting combustion, including sending of signals to the individual combustors 16, including providing control of, for example, the fuel/air ratio at the combustors 16.

To prevent ingress of combustion gas into the cavity 36 the waveguide 30 is sealed from the flow path 17 by closing the first waveguide end with a membrane 58 capable of withstanding typical high temperatures of the combustion gas, e.g., up to 1,200° F. (650 C). However, the first waveguide end 32 is also relatively transmissive to effect propagation and reflection of acoustic measurement signals from the transmitter unit 44, through the first waveguide end 32, into a measurement region 60 in the flow path 17, back through the first waveguide end 32 and into the waveguide cavity 36 for sensing by the receiver unit 46. As indicated with an arrow 64, for an acoustic signal generated with the transmitter unit 44, a measurable portion of the transmitted signal is reflected from a part of the wall 40 to return through the first waveguide end 32 and into the cavity 36 for sensing by the receiver unit 46.

Consistent with the frustoconical shape of the cavity 36, a portion along the waveguide first end 32 has an interior circular shape of diameter, D, and the membrane 58 at least spans the diameter, D, to completely cover and seal the first end 32. The membrane 58 may be bonded about the first end of the waveguide, e.g., by a weld or braze, to extend across an exterior region surrounding the waveguide end. Numerous other arrangements may effect the seal, including use of a threaded ring which matingly engages another threaded body to press and secure the membrane against a surface adjoining the interior circular shape of diameter, D, along the first end 32, optionally with a gasket or sealing member there between. With this or another mechanical coupling arrangement the membrane 58 is removable for maintenance or replacement. In other embodiments, the membrane may extend across the mounting sleeve 42 by, for example, attachment across an opening near the interface 62 between the sleeve 42 and the wall 40 or by attachment across a wall opening. The membrane may be removable for maintenance or replacement. Absent a hermetic seal between the membrane 58 and the cavity 36, when a cooling system sends high pressure air from the turbine compressor into the cavity 36, there may be slight leakage of relatively high pressure cooling air from the waveguide, past the membrane 58, and into relatively lower pressure combustion gas in the flow path 17.

The membrane may comprise titanium or a nickel alloy of sufficient thickness to assure integrity under turbine operating conditions while also permitting satisfactory acoustic transmission properties, e.g., preferably less than 10 dB attenuation, to assure a satisfactory signal to noise ratio. In one embodiment the membrane comprises an alloy in the Inconel 600 series (e.g., 601, 610 or 625) having a thickness in a range of 200-300 microns. In the illustrated embodiments the membrane 58 acts as a secondary diaphragm of an acoustic transmitter similar to an electro-dynamic speaker. With the exemplary dimensions of the membrane and the exemplary attachment methods the membrane 58 can reproduce the signal without unacceptable distortion relative to that originating from the transmitter unit 44.

The time-of-flight of the portion of the signal traveling between the transmitter unit 44 and the receiver unit 46 is used to determine a temperature value for of the combustion gas travelling through the region 60 at the time of measurement. The temperature determination is based on the principle that the speed of sound in a gas changes as a function of temperature. For a determined or known composition of the gas, it is possible to determine the temperature of the gas based on the measured time for an acoustic signal to travel the distance between the transmitter unit 44 and the receiver unit 46, i.e., based on the speed of the sound signal traveling through the gas.

The acoustic temperature measurement system 24 includes a cooling arrangement to control the temperature of the waveguide cavity 36, the waveguide wall 38 and acoustic instrumentation such as the transmitter unit 44 and the receiver unit 46. A relatively cool fluid 70 is provided into and around the waveguide 30 through an inlet port 74 which extends into the cavity 36. The fluid 70 exits the waveguide via an outlet port 78 which also extends into the cavity 36. The inlet port 74 is positioned close to the waveguide first end and the outlet port 78 may be positioned approximately midway between the first and second waveguide ends causing the fluid 70 to travel in a direction away from the first end 32 and toward the second end 34. However, the direction of flow may be reversed. This arrangement predominantly sends the fluid 70 through a portion of the cavity proximate the waveguide first end. The inlet port may be in such close proximity to the membrane 58 that the cool fluid 70 impinges on the membrane. The inlet port 74 may also include or only include an opening to inject the fluid 70 into the channel, C, and the outlet port 78 may also include an opening to allow the cooling fluid 70 to exit the channel, C. This arrangement further facilitates cooling exterior portions of the waveguide closest to the flow path 17. In still other designs the inlet and exit ports may only send the cooling fluid 70 directly into the channel, C, but the waveguide wall 38 includes a series of ingress ports 82 near the first waveguide end through which the fluid 70 is sent into the cavity. The wall also includes a series of egress ports 83 through which fluid 70 in the cavity 36 returns into the channel, C. Multiple cooling paths have been illustrated for the embodiment shown in FIG. 2. Other embodiments may incorporate one of these apart from or in combination with one or more other cooling path designs for the waveguide and acoustic instrumentation, e.g., sending cooling fluid 70 through the cavity 36 only, or only providing cooling of the waveguide wall with the channel C, or providing multiple ones of the cooling arrangements such as cooling through both the channel C and the cavity by sending fluid 70 through the ports 82, 83. In the past, waveguides suitable for acoustic temperature measurement systems have been cast or machined from steel in order for the end portion of the waveguide adjoining the flow path to withstand high temperatures ranging, for example, up to 650 C. However, with the waveguide having a thermal conductivity typical of a metal, it has been difficult to limit thermal conduction to prevent thermal energy present in the adjoining flow path 17 from eventually elevating the temperature in the vicinity of the acoustic instrumentation. This is a concern even when the instrumentation is at the end 34 of the waveguide farthest away from the flow path 17.

Figure 3:
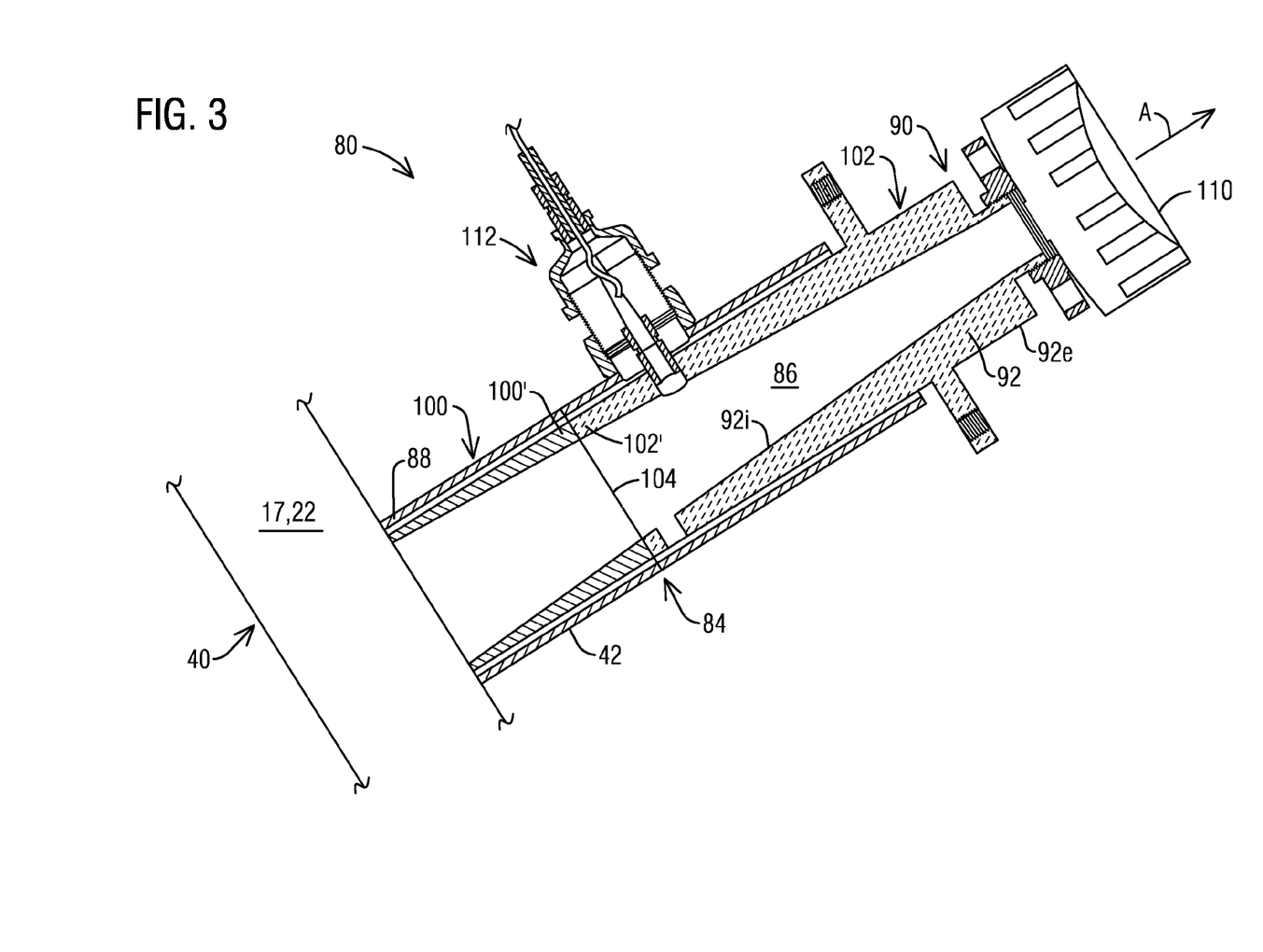
FIG. 3 illustrates features of an acoustic temperature measurement system according to another embodiment with a waveguide comprising first and second sections comprising having different materials properties.

The partial view of FIG. 3 illustrates an acoustic temperature measurement system 80 comprising a hybrid waveguide 84, the features of which may be incorporated into the embodiment of FIG. 2, or in other acoustic temperature measurement systems that do not physically isolate the waveguide cavity from combustion gas in the adjoining flow path. The cavity 86 of the waveguide is a tapered cavity which extends symmetrically along an axis, A, between first and second waveguide ends 88, 90. The waveguide wall 92, formed along both sections 100, 102 and about the cavity 86, has a cylindrically shaped exterior wall surface 92e and has, along an interior surface 92i, a tapered shape complementary to that of the tapered cavity 86.

The exemplary first waveguide end 88 is in open communication such that the flowing combustion gas may influence state variables in the cavity 86. Specifically, there may be an influx of combustion gas into the cavity 86 and a transfer of thermal energy into the waveguide wall 92 and cavity (e.g., by conduction or convection) toward the second end 98. The gas turbine engine 10 may comprise a plurality of waveguides incorporating the features of the waveguide 84, each located at a position of interest along a wall 40 in the flow path 17. The first waveguide end 88 is positioned within a cylindrically shaped mounting sleeve 42 that extends outward from the wall 40 and the second waveguide end 90 extends beyond the mounting sleeve 42. As described for the embodiment of FIG. 2, the mounting sleeve 42 may have an inside diameter substantially larger than the outside diameter of the exterior wall 92e to provide a cooling channel, C.

The waveguide 84 comprises first and second connected sections 100 and 102. In one embodiment the first section 100 is formed of high temperature metal, e.g., a stainless steel alloy, and extends between a central transition region 104 between the two sections 100, 102 to the waveguide end 88 which adjoins the flow path 17. More generally, the first section 100 may be formed of a material composition predominantly comprising a metal or ceramic material and having a melting point exceeding 800 C. The waveguide end 88 of the first section 100 is connected along a wall 40 of a flow path 17 for fluid communication or acoustic communication with the combustion gas.

The second waveguide section 102 is a body formed of an electrically isolating material having low thermal conductivity properties, e.g., those of a thermoplastic polymer or a ceramic material, perhaps less than 0.4 watts/m-K. The waveguide section 102 may have a volume resistivity greater than $10^{15}$ ohm-cm, More generally, the second section 102 is formed of an electrically isolating material composition having a lower thermal conductivity than the material of the first section 100 (e.g., by eighty to five hundred times). Numerous ceramics may be suitable for the material of the second section 102 including ceramics containing zirconium oxide ($ZrO_2$) and which may be partially stabilized with yttrium. The material of the second section 102 predominantly comprises nonmetal.

In one series of embodiments the material of the first section has a higher melting temperature than the material of the second section. In another series of embodiments the material of the second section 102 has greater electrically isolating properties than the material of the first section 100. That is, the material of the second section 102 is more electrically insulative than the material of the first section 100. In a third series of embodiments the material of the second section 102 has a lower thermal conductivity than the material of the first section 100. In other embodiments, the material of the first section 100 may be a ceramic or cermet, the material of the second section 102 may be a ceramic or cermet and the sections 100 and 102 may both comprise a ceramic or cermet.

The section 102 extends from the central transition region 104 to the second waveguide end 90. Per the embodiment shown in FIG. 3, an acoustic transmitter 110 may be attached along the second waveguide end 90. An acoustic receiver 112 may also be positioned in the second waveguide section 102, i.e., in an operating environment which benefits from the electrically isolating and low thermal conductivity properties of the second waveguide section 102. This enables the acoustic instrumentation to operate under lower temperature conditions than present along the first waveguide section 100.

The material of the first section 100 exhibits strength and stability while directly exposed to high temperatures present in an adjoining flow path 17 during turbine operation. The section 102 exhibits low thermal conductivity to help limit thermal conduction between the transition region 104 and the waveguide second end 90, and limit the maximum temperature to which acoustic instrumentation mounted in the second section is subjected during turbine operation. Use of an electrically non-conducting material in the second section 102 of the hybrid waveguide 84 is advantageous when using an acoustic transmitter which generates a high voltage spark. The electrically isolating waveguide section 102 insulates the receiver electrically and magnetically isolates the receiver from EMF generated by the spark. Also, grounding concerns are removed because the sensors are isolated from the engine, thereby avoiding creation of ground loops.

The connected sections 100, 102 of the waveguide 84 may be formed in multiple ways. In one series of embodiments the waveguide is fabricated in an additive manufacturing process that incorporates distinct material compositions to provide different performance objectives in the adjoining sections.

Portions of the waveguide can be built up in discrete layers, e.g., 10 to 30 microns thick, with a graded deposition of blended powders to transition from a first region predominately comprising a first material (e.g., a metal) to a second region predominately comprising, for example, a thermoplastic or ceramic material that isolates acoustic instrumentation from temperature excursions and damage due to heat conduction. Particles of differing material types may be used when depositing the various layers, $L_i$, with a ratio of the types of materials changing between layers to produce a functional gradient in the transition region 104. Use of the thermoplastic or ceramic material to form the second section 102 also prevents electrical and magnetizing effects prevalent in a waveguide made entirely of metal. This and other forms of hybrid waveguides can be manufactured with shorter fabrication times (e.g., less than half the time) while improving the overall performance of the acoustic temperature measurement system.

Figure 4:
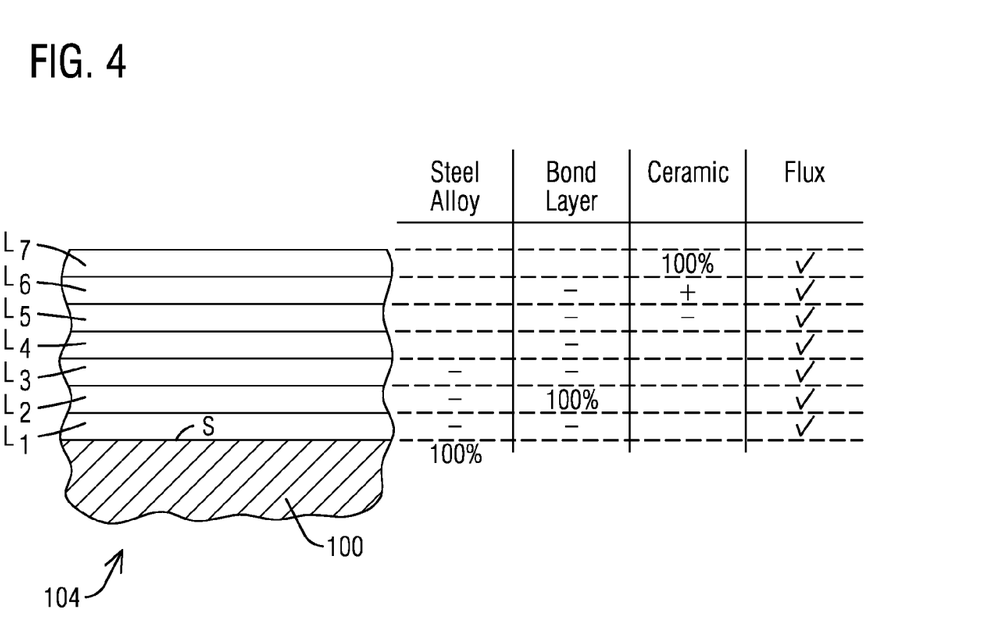
FIG. 4 schematically illustrates a series of sequentially formed layers $L_i$ along a portion of a transition region between the first and second sections of a waveguide wall shown in FIG. 3.

One such process builds a portion of the waveguide 84, e.g., the transition region 104, with a sequence of discretely formed layers, $L_i$, one layer over another layer, which introduce a gradient in material composition. Functionally graded materials are characterized by a gradual change in composition over a volume. Such materials avoid the disadvantages sometimes associated with abrupt material changes. A metal-ceramic gradient composition is described in U.S. Pat. No. 6,322,897 as being formed by sintering a packed bed of powder having a graded composition across the bed.

In one embodiment the first section 102 is formed of a stainless steel alloy with casting or machining processes. A bond layer of material is applied directly against the steel alloy material of the first section 100. This may comprise an alloy powder thickness of 1-4 mm under a flux powder thickness of 2-5 mm. Exemplary layer thickness variants, flux types, laser types and typical power level for processing are described in US2015/0030871 incorporated herein by reference. After processing a layer of slag is removed prior to application of subsequent layers. After formation of the bond layer graded sequence of deposited layers is applied to transition the material composition to predominately or entirely ceramic. See FIG. 4 which illustrates a portion of the transition region 104 in which such layers $L_i$ extend along a plane perpendicular to the axis, A. The layers $L_i$ may be deposited by a thermal spray process, such as High Velocity Oxy-Fuel (HVOF) or Air Plasma Spray (APS). As described in US2015/0030871, the layers $L_i$ may be formed by depositing layers of powder comprising materials which result in a desired percent composition. Specifically, the above described bond layer, referenced as layer $L_1$, may comprise particles of the metal alloy present in section 100 and a flux material. Generally, this first layer $L_1$ is formed on a surface S of the section 100 comprising the alloy (e.g., steel). The surface, S, is also perpendicular to the axis, A. The bond layer $L_1$ may incorporate material having thermal barrier properties (e.g., MCrAlY). Subsequent layers beginning with the layer $L_2$ change in proportion of bond layer material to ceramic material from a relatively higher concentration of bond coat material in layer $L_2$ to a relatively higher concentration of ceramic material, where the concentration of ceramic material increases with each subsequent layer $L_{i+1}$ deposited over a prior layer $L_i$ until the last in the sequence of graded layers (e.g., $L_7$) comprises 100 percent ceramic material or another composition consistent with desired composition of the section 102. With the transition region so formed the section 102 may also be fabricated with an additive manufacture technique (not shown), e.g., continued deposition of materials and processing to form a series of layers comprising the desired composition of the section 102.

FIG. 3 also includes a table showing relative proportions of alloy particles, bond layer particles and ceramic particles in each respective layer associated with the transition region 104. The column titled "Flux" indicates that each layer is deposited using a powder deposition process as described in U.S. 2015/0030871, such as laser melting or laser sintering.

Layers $L_1$ through $L_7$ are only exemplary of a graded system of layers to transition the composition of a structure formed by powder deposition of a plurality of layers of material with the composition of the layers varying along the axis, A. Different combinations and quantities of these types of layers or other types of layers may be included in other embodiments. For example, in one embodiment the sequence may add or remove layers from those which are illustrated. Multiple steps of more gradually changing composition ratios may be used in other embodiments. Some layers may include additional alloy composition or bond layers. Layers may be of equal or varying thicknesses. Multiple compositions of alloy material, bond layer materials or ceramic materials may be used in a sequence which forms the transition region 104.

The sections 100 and 102 of the waveguide 84 may also be fabricated as discrete components which are subsequently joined together by, for example, fashioning mating portions 100' and 102' with the transition region 104 being an interface between the two sections. Joining at the interface may be had with interlocking patterns formed on the mating portions or with a clamping collar or by encasing the components to establish a mechanical connection and stability during engine operation.

In other embodiments, the waveguide 84 of FIG. 3 may also be isolated from the hot combustion gas by an acoustically transparent membrane as described in FIG. 2. Moreover, one or more active cooling circuits may be incorporated to provide active cooling of the entire waveguide 84 or only portions of the waveguide 84, such as only the first section 100. Other embodiments may include a first section formed of metal, ceramic, ceramic matrix composite, cermet or other material capable of operation under high temperature conditions, and a second section may be formed of materials such as a ceramic or thermoplastic to provide electrical, magnetic and/or thermal isolative properties. The acoustically transparent membrane 58 may be located at or near the junction of the first and second sections, in lieu of or in addition to locating such a membrane at the first end 32 of the cavity.

There has been described an acoustic apparatus and method for accurate, non-intrusive characterization of hot gas flow temperature, velocity and mass flow. The disclosed system may incorporate multiple transmitters and multiple receiving sensors along the flow path of a combustion gas which exits the combustor section of a turbine engine. Placement of the acoustic transmitters and receivers within a waveguide cavity, which is sealed to prevent ingress of the hot combustion gas, isolates the acoustic devices from very high operating temperatures which would impose more stringent requirements for operation or more stringent cooling requirements to prevent more frequent instrumentation failures. Furthermore, the apparatus and method enable a more accurate determination of temperature information because the acoustic instrumentation is isolated within the waveguide. Thus any cooling fluid being circulated to protect the instrumentation does not extend into the combustion gas flow path. Also, because the chamber 36 is isolated from the flow path, cooling methods can incorporate cooler air that has been used when the instrumentation is directly in the flow path.

In one series of embodiments there have been described a method of operating a gas turbine engine which exhausts combustion gas along a flow path and a gas turbine engine incorporating an apparatus for controlling turbine operation based on monitoring combustion gas operating temperature and other parameters such as velocity and mass flow rate.

The method provides time of flight information based on propagation of an acoustic signal to determine an operating temperature of the combustion gas while the gas passes through a measurement region in the flow path. A waveguide is positioned for isolation from flow of the combustion gas while injecting the acoustic signal into a measurement region. Temperature within the waveguide is limited, relative to the combustion gas operating temperature, by positioning an acoustically transmissive physical barrier between the waveguide and the measurement region to prevent movement of the combustion gas from the measurement region into the waveguide while permitting transmission of the acoustic signal from the waveguide into the measurement region to acquire the time of flight information.

In one embodiment at least one device is positioned for transmitting the acoustic signal from the one device into the measurement region, and detecting return of the acoustic signal into the waveguide after the signal is reflected from a surface in the measurement region. Time of flight information is determined for the transmission and return of the acoustic signal, and the operating temperature is determined based on the time of flight information. Generally, the waveguide may comprise cavity adjoining the flow path along which instrumentation is placed to transmit the acoustic signal into the measurement region and monitor return of the acoustic signal after reflection from the measurement region. In one embodiment positioning the acoustically transmissive physical barrier may include positioning a membrane along an end of the waveguide to prevent flow of combustion gas into the waveguide. The waveguide seals the cavity from receiving combustion gas directly from the flow path. The temperature in the waveguide may be limited by injecting a gas into the waveguide to flow between the first and second waveguide ends.

There has been described an acoustic temperature measurement system for providing acoustic time of flight information for combustion gas in a gas turbine engine. Measurement is based on propagation of an acoustic signal to determine an operating temperature of the combustion gas while the gas passes through a measurement region in the flow path. A waveguide has first and second ends and a cavity extending between the first and second ends of the waveguide. The first end is positioned to adjoin the flow path for injection of the acoustic signal into the measurement region. An acoustically transmissive physical barrier is positioned between a portion of the waveguide and the measurement region to prevent movement of combustion gas from the measurement region into the waveguide while permitting transmission of the acoustic signal from the waveguide into the measurement region. The physical barrier is positioned to limit temperature within the waveguide, relative to combustion gas operating temperature in the flow path.

There has been described a gas turbine engine including an apparatus for controlling operation based on monitoring combustion gas operating temperature in a measurement region along a flow path. Measurement is based on determining time of flight information for propagation of an acoustic signal through the measurement region. The engine includes a combustor section and a turbine section along which a flow path extends from the combustor section and a waveguide having first and second opposing ends. The first end adjoins the flow path to enable injection of the acoustic signal into the flow path while the waveguide remains isolated from flow of the combustion gas therein. The waveguide includes a barrier layer across the first end. Acoustic instrumentation, providing the functions of an acoustic transmitter and a receiver, is positioned along an interior wall of the waveguide to generate the acoustic signal and sense receipt of the acoustic signal after reflection from the measurement region. The barrier layer may include a membrane comprising titanium or a nickel alloy.

There has also been described a waveguide for use in a gas turbine engine for determining time of flight information for propagation of an acoustic signal through a measurement region in a flow path carrying engine combustion gas. The waveguide comprises a body having first and second ends and a tapered cavity extending between the first and second ends, with the first end including a barrier layer so that when the first end is positioned to adjoin the flow path to inject the acoustic signal into the flow path, the cavity remains isolated from flow of the combustion gas along the flow path. The waveguide may also include acoustic instrumentation positioned along an interior wall of the waveguide to provide for generation of the acoustic signal and propagation of the acoustic signal into the measurement region. The waveguide may also include cooling passages along a wall thereof to control temperature of the acoustic instrumentation. The cooling passages may include an inlet port and an outlet port positioned to pass the cooling fluid through a portion of the chamber. The cooling passages may include an inlet port and an outlet port each positioned to circulate cooling fluid through a channel formed along an exterior surface of the waveguide.

A hybrid waveguide has also been described. In one series of embodiments a hybrid waveguide is provided for placement adjacent a flow path for hot combustion gases in a gas turbine engine. The waveguide is a body member with first and second opposing ends. The body member includes a first section formed of a first material extending from a transition region to the first end and a second section formed of a second material extending from the transition region to the second end. The first material predominantly comprises a metal. The second material comprises an electrically isolating material having a lower thermal conductivity (e.g., fifty to one thousand times lower) than the material of the first section. In one example embodiment the first material predominantly comprises a steel alloy.

The second material may predominantly or entirely comprise a thermoplastic material or a ceramic formulation. The transition region may comprise a graded sequence of layers that transition the composition of the waveguide from the first material in the first section to the second material in the second section. The first material in the first section may include or be entirely a composition which predominantly comprises metal and the second material in the second section include or entirely be a composition having a lower thermal conductivity than that of the first material composition.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the claims which now follow.

The claimed invention is:

1. A hybrid waveguide for placement adjacent a flow path for hot combustion gases in a gas turbine engine, comprising:
a body member having first and second opposing ends, the body member comprising a first section formed of a first material extending from a transition region to the first end and a second section formed of a second material extending from the transition region to the second end, the first material having a higher melting temperature than the second material,
wherein the transition region comprises a graded sequence of layers that transition the composition of the waveguide from the first material in the first section to the second material in the second section.

2. The waveguide of claim 1 wherein the second material has higher electrically isolating properties than the first material.

3. The waveguide of claim 1 wherein the first material predominantly comprises a metal, a ceramic or a cermet.

4. The waveguide of claim 1 wherein the second material predominantly comprises a ceramic, a cermet or a thermoplastic material.

5. The waveguide of claim 1 wherein the first material predominantly comprises a steel alloy or an alloy of nickel or an alloy of cobalt.

6. The waveguide of claim 1 wherein the first material in the first section includes a composition which predominantly comprises metal and the second material in the second section comprises a composition having a lower thermal conductivity than that of the first material composition.

7. The waveguide of claim 1 wherein the composition of the second section predominantly comprises a composition having a lower thermal conductivity than that of the first material composition.

8. The waveguide of claim 1 further including an acoustic transmitter positioned in the second section along a wall of the waveguide to generate the acoustic signal.

9. The waveguide of claim 1 further including a receiver positioned in the second section along a wall of the waveguide to sense the acoustic signal.

10. The waveguide of claim 1 wherein the first section is fabricated as a discrete component by a casting process or a machining process.

11. The waveguide of claim 1 wherein the first section is fabricated as a discrete component and the second section is fabricated as a discrete component separate and distinct from the first section and, subsequently, the first and second sections are joined together.

12. The waveguide of claim 11 wherein the first and second sections are joined together by mating portions of each along an interface provided in the transition region.

13. A hybrid waveguide for placement adjacent a flow path for hot combustion gases in a gas turbine engine, comprising:
a body member having first and second opposing ends, the body member comprising a first section formed of a first material extending from a transition region to the first end and a second section formed of a second material extending from the transition region to the second end, wherein the first material is a metallic alloy and the second material predominantly comprises material taken from the group consisting of a thermoplastic material, a ceramic and a cermat,
wherein the transition region comprises a graded sequence of layers that transition the composition of the waveguide from the first material in the first section to the second material in the second section.

14. A hybrid waveguide for placement adjacent the flow path of a gas turbine engine, the waveguide having first and second opposing ends, the waveguide comprising:
a first section formed of a first material extending from a transition region to the first end and a second section formed of a second material extending from the transition region to the second end, the first material predominantly comprising a metal or a ceramic material and having a melting temperature above 700 degrees C., and wherein the second material is an electrically isolating material; and
an acoustic transmitter positioned in the second section along a wall of the waveguide to generate the acoustic signal,
wherein the transition region comprises a graded sequence of layers that transition the composition of the waveguide from the first material in the first section to the second material in the second section.

15. The waveguide of claim 13 further including a receiver positioned in the second section along a wall of the waveguide to sense the acoustic signal.

16. The waveguide of claim 13 wherein the first section is fabricated as a discrete component by a casting process or a machining process.

17. The waveguide claim 13 wherein the first section is fabricated as a discrete component and the second section is fabricated as a discrete component separate and distinct from the first section and, subsequently, the first and second sections are joined together.

18. The waveguide of claim 17 wherein the first and second sections are joined together by mating portions of each along an interface provided in the transition region.

19. The waveguide of claim 14 wherein the second material is a thermoplastic material having a lower thermal conductivity than the first material.

* * * * *